United States Patent
Rinner

(10) Patent No.: US 6,783,004 B1
(45) Date of Patent: Aug. 31, 2004

(54) KIT OF MEDICAL TOOLS FOR REMOVING SCREWS

(75) Inventor: James A. Rinner, Racine, WI (US)

(73) Assignee: Pilling Weck Incorporated, Horsham, PA (US)

( * ) Notice: Subject to any disclaimer, the term of this patent is extended or adjusted under 35 U.S.C. 154(b) by 35 days.

(21) Appl. No.: 10/281,926

(22) Filed: Oct. 29, 2002

Related U.S. Application Data

(60) Provisional application No. 60/411,290, filed on Sep. 17, 2002.

(51) Int. Cl.$^7$ .............................................. B65D 85/00
(52) U.S. Cl. ...................... 206/368; 206/370; 206/63.5
(58) Field of Search ................................ 206/363, 368, 206/369, 370, 63.5, 438

(56) References Cited

U.S. PATENT DOCUMENTS

| | | | |
|---|---|---|---|
| 2,472,028 A | 5/1949 | Son | |
| 4,090,606 A | 5/1978 | Dawson | 206/223 |
| 4,501,363 A | 2/1985 | Isbey | 206/570 |
| 4,595,102 A | 6/1986 | Cianci | 206/572 |
| 4,596,329 A | 6/1986 | Eldridge | 206/370 |
| 4,828,113 A | 5/1989 | Friedland | 206/570 |
| 5,172,810 A | * 12/1992 | Brewer | 206/369 |
| 5,174,453 A | 12/1992 | Stoeffler | 206/570 |
| 5,251,751 A | 10/1993 | Prussen | 206/338 |
| 5,289,919 A | 3/1994 | Fischer | 206/571 |
| 5,379,887 A | 1/1995 | Conley | 206/459.5 |
| 5,417,585 A | 5/1995 | Morin | 439/488 |
| 5,762,202 A | 6/1998 | Atad | 206/756 |
| 5,868,250 A | 2/1999 | Brackett | 206/363 |
| 6,158,437 A | 12/2000 | Vagley | 128/898 |
| D442,697 S | 5/2001 | Hajianpour | D24/229 |
| 6,368,565 B1 | * 4/2002 | Michaelson et al. | 422/300 |

* cited by examiner

*Primary Examiner*—Jacob K. Ackun, Jr.
(74) *Attorney, Agent, or Firm*—Arthur J. Hansmann

(57) ABSTRACT

A kit of medical tools for removing screws from a patient in surgical procedures, including both the kit and the method of arranging the kit and its bits and tools. There are two removable trays in a container, one for the bits and one for the tools, and the trays stack upon the other in the container. Corresponding indicia are on both the bits and the supporting trays so the bits can be organized and readily selected by the surgeon, and an abutment aligns the bits in resilient grippers on the bit tray.

13 Claims, 7 Drawing Sheets

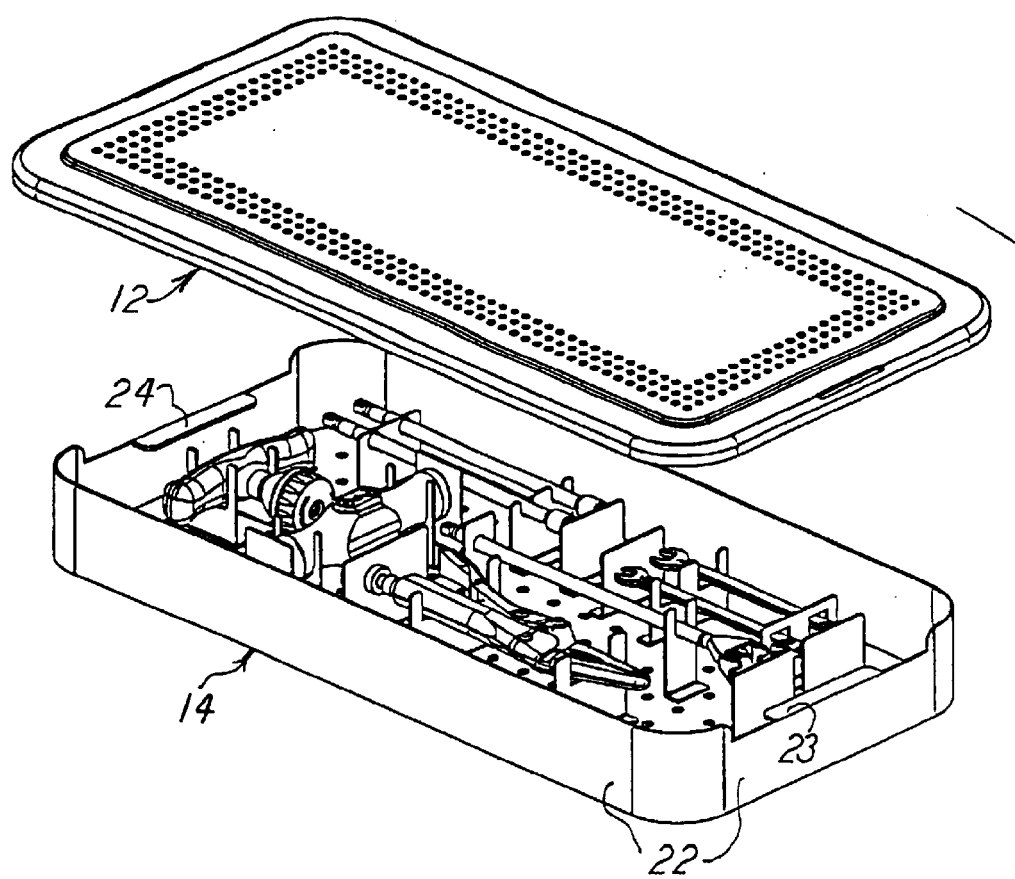
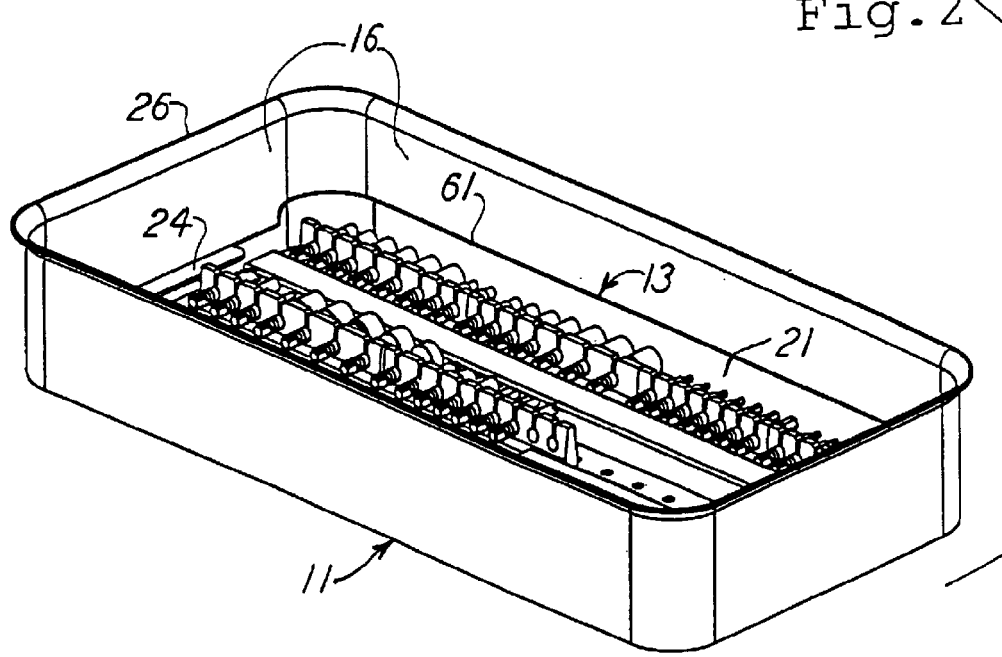
Fig. 2

KIT OF MEDICAL TOOLS FOR REMOVING SCREWS

This application claims the benefit of U.S. Provisional application No. 60/411,290 filed on Sep. 17, 2002.

This invention relates to an orthopedic implant removal system, and particularly to a kit of medical tools for removing screws from a patient's bone, and a method of kit arrangement. The kit includes both the bits for engaging the screws and nuts and the universal drivers of the bits for the torquing, and it includes other removal tools.

BACKGROUND OF THE INVENTION

The prior art is already aware of trays for containing medical tools for medical procedures. The trays can be separately moved, and the tray and its tool contents are then individually available for use. The prior art is also aware of surgical tool trays for supporting surgical tools and having thereon indicia identifying the tools.

Today there are many spinal implant manufacturers. Also, where spinal fusion or fixation does not remain reliable, there must be revision. Screws, rods, plates, hooks and the like implants are installed, but need revision. When the surgeon is into the procedure, he should have the necessary tools for the implant involved. Usually the screws need to be removed, and that requires the precise tool to fit the screw in accord with the task underway. That means a need for immediate access to the accommodating tools.

The implanted screws can be cut and taken out, but that undesireably destroys the fusion. Additionally screws might be added, but that too presents its obvious problems.

The present invention responds to the problems of fusion revision, and it does so with a kit of tools and tool bits for removal the myriad of today's implant screws by various manufacturers. This kit is universal for removal of both the screws and nuts through ready access by the surgeon.

The kit includes both male and female nut removers. There are custom removers, and like tools which are needed for the removal. So this kit includes the bits, tools, extenders, yokes for restraining the bone, pliers and the like. The bits include indicia thereon for revealing their functions and sizes, and the kit trays for the tools and the bits have indicia for the information.

So in a single kit the surgeon has all the bits and tools needed when the surgeon in well into the removal procedure. There is no unnecessary delay to find the tool that fits the screws already in the patient and awaiting revision.

A reading of the following description and a viewing of the drawings will reveal these aforementioned objectives, along with other objects that become apparent.

BRIEF DESCRIPTION OF THE DRAWINGS

FIG. 2 is an exploded perspective view of the kit of FIG. 1.

DETAILED DESCRIPTION OF THE PREFERRED EMBODIMENT AND METHOD

Figure 1:
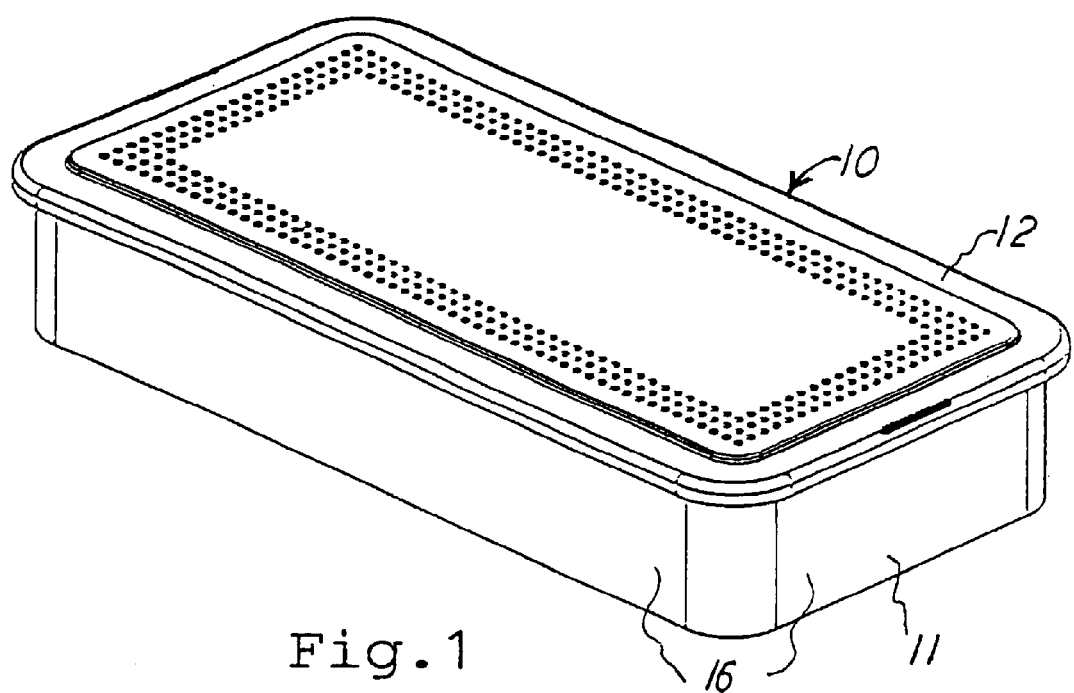
FIG. 1 is a perspective view of a kit of this invention, in its closed position.
Figure 3:
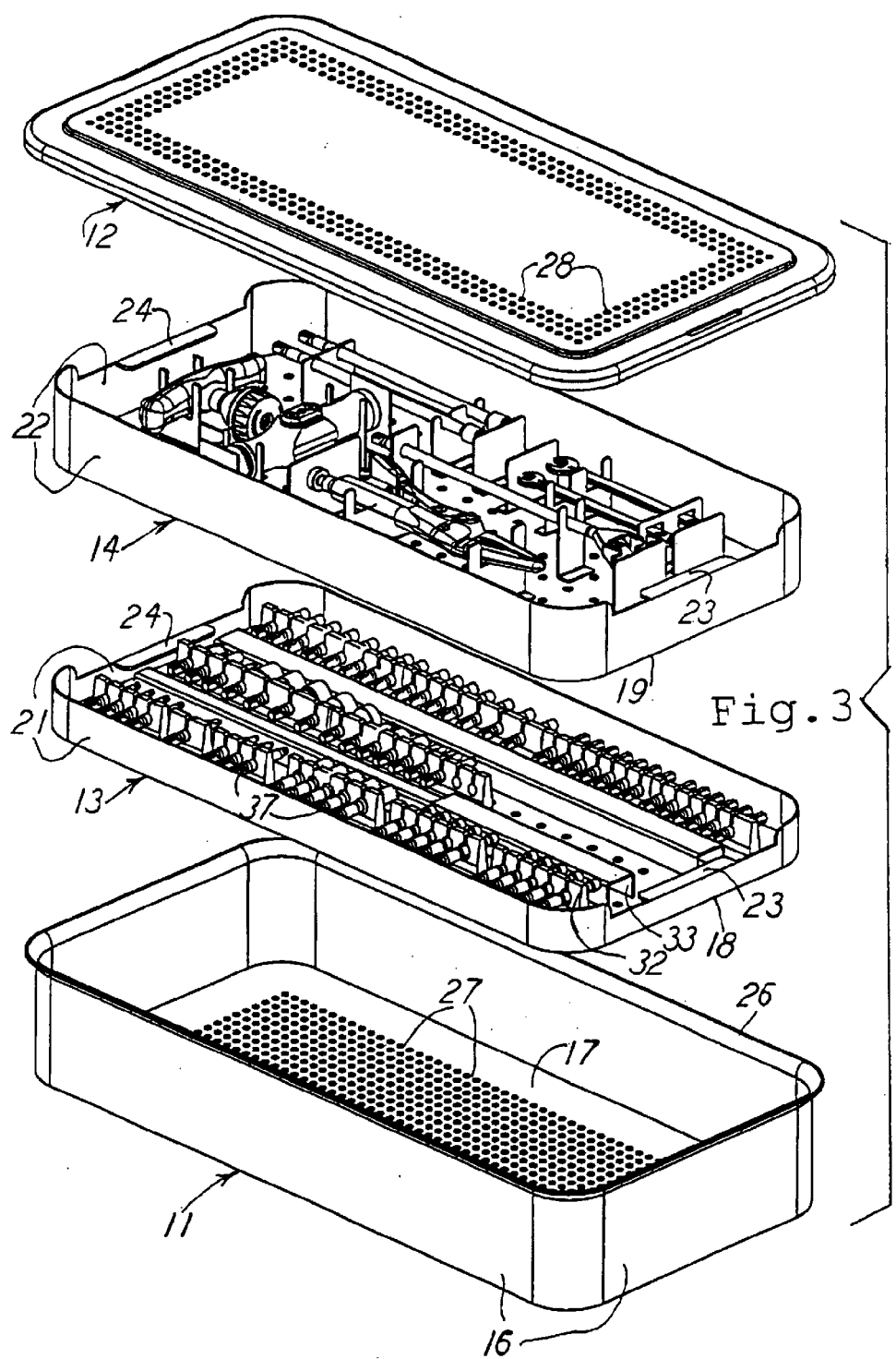
FIG. 3 is an exploded perspective view similar to FIG. 2 but with the kit in greater separation.

FIG. 1 shows a closed container presenting the kit 10 of this invention, which has a base 11 and a top cover 12. Thus the kit 10 is completely enclosed and it includes the implements of this invention for the usages mentioned. It is capable of the removal of a majority of the usual implants in bone. In actuality, the kit 10 includes over seventy bits for standard metric and English drives, hexalobe, broken and stripped screw removers, and custom implant specific bits. Also included are drive extensions, ratcheting drive T-handle, multi-axial handle, counter-torque wrench, combination. wrenches, and needle-nose locking pliers. So all the tools necessary for the myriad of conditions are included in the single kit.

The other drawings show the contents of the base 11, and it will generally be seen that there are two trays 13 and 14 which are basically planar and extend substantially throughout the girth of the base 11 and snugly within the upstanding four walls 16 of the base 11. All three parts 11, 13, and 14 are substantially the same shape in that they all have a respective planar floor 17, 18 and 19. Also, the trays 13 and 14 have respective upstanding four enclosing walls 21 and 22, comparable to the base walls 16.

So each of the parts 11, 13, and 14 present a similar configuration of a container with a floor and sides walls and an upwardly faced opening. The trays 13 and 14 each include handle portions 23 and 24 which extend inwardly on each tray and are available for being gripped by the user to lift and lower the trays relative to the other parts. Thus, the trays 13 and 14 can be removed and replaced relative to the base 11 when the cover 12 is removed from the base 11. Cover 12 is essentially of a planar configuration, and it can be snap fit relative to the base 11 and onto the upper rim 26 of the base 11.

Both the base 11 and the cover 12 have perforations, such as at 27 and 28, respectively, and thus there is aeration for the base 11 and its contents. Also, the trays 13 and 14 have perforations 29 and 31.

Figure 4:
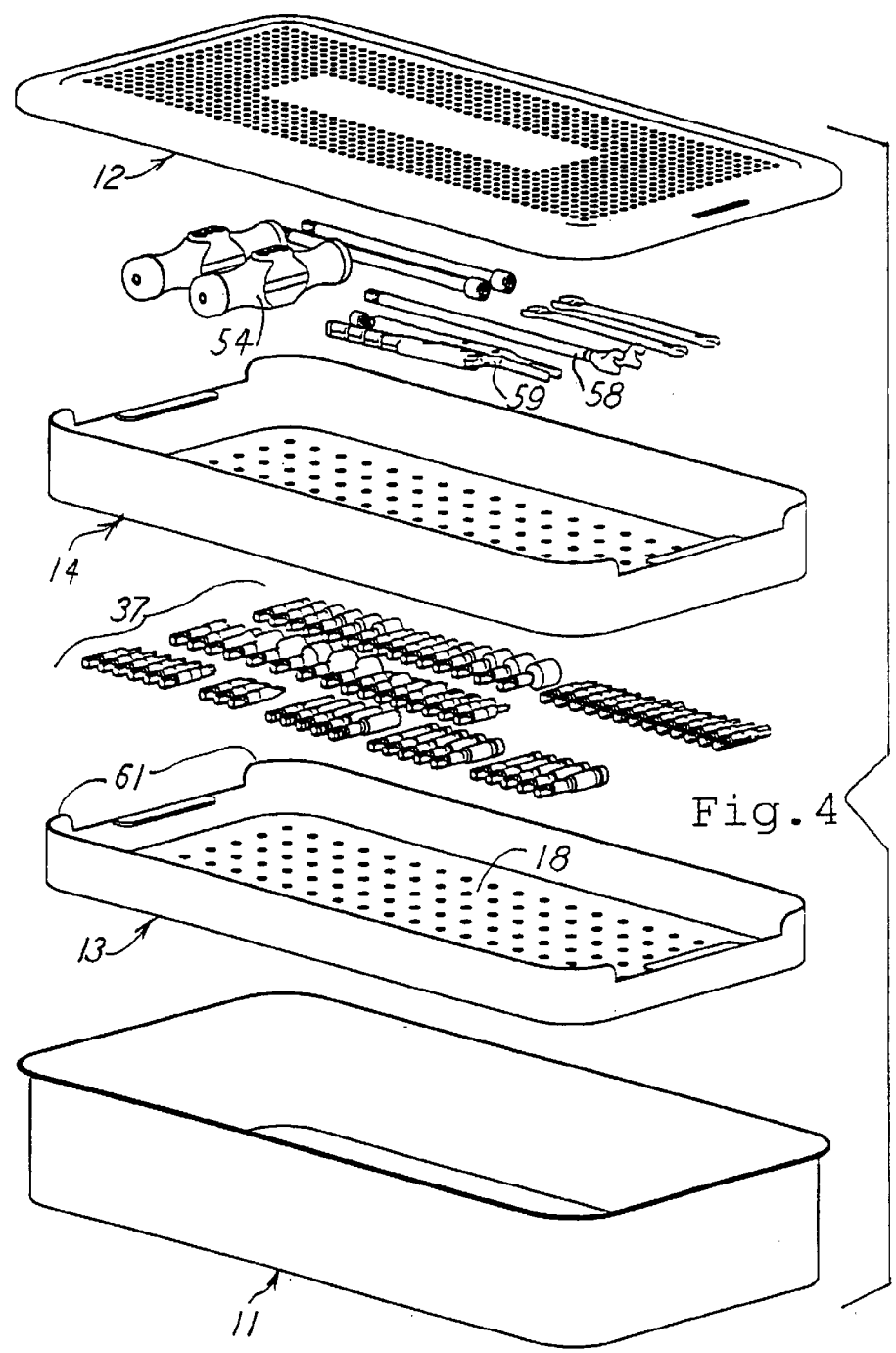
FIG. 4 is an exploded perspective view similar to FIG. 3 but with the kit in greater separation, and with portions removed

Tray 13 has upstanding supports, such as support 32, for example, attached to the floor 18 for restraining the movement of items on the tray 13. The tray 13 also has abutments 33 for restraining movement. Tray 14 has upstandinq supports 34 and 36, for example, attached to the floor 19 for restraining the movement of items on the tray 14. For tray 13, there are a considerable number of tool bits, all distinct from each other but generally designated 37, and best shown in FIG. 4 as a separated group, for display.

The bits 37 can be of a considerable total number, such as seventy in total number, and each one is unique and distinct from the others. Each has a screw engaging end 38, such as a socket or multi-sided end or a screw engager or reamer or bone cutter, such as the variety shown in FIGS. 6 and 7. One end of each bit 37 also has a drivable end 39, such as the square ends shown and with the ball detent shown for snap connection and release relative to a driving handle or member by which the bits 37 are rotatable. Again, FIG. 7 shows the shapes and variety of the bits 37.

Figure 7:
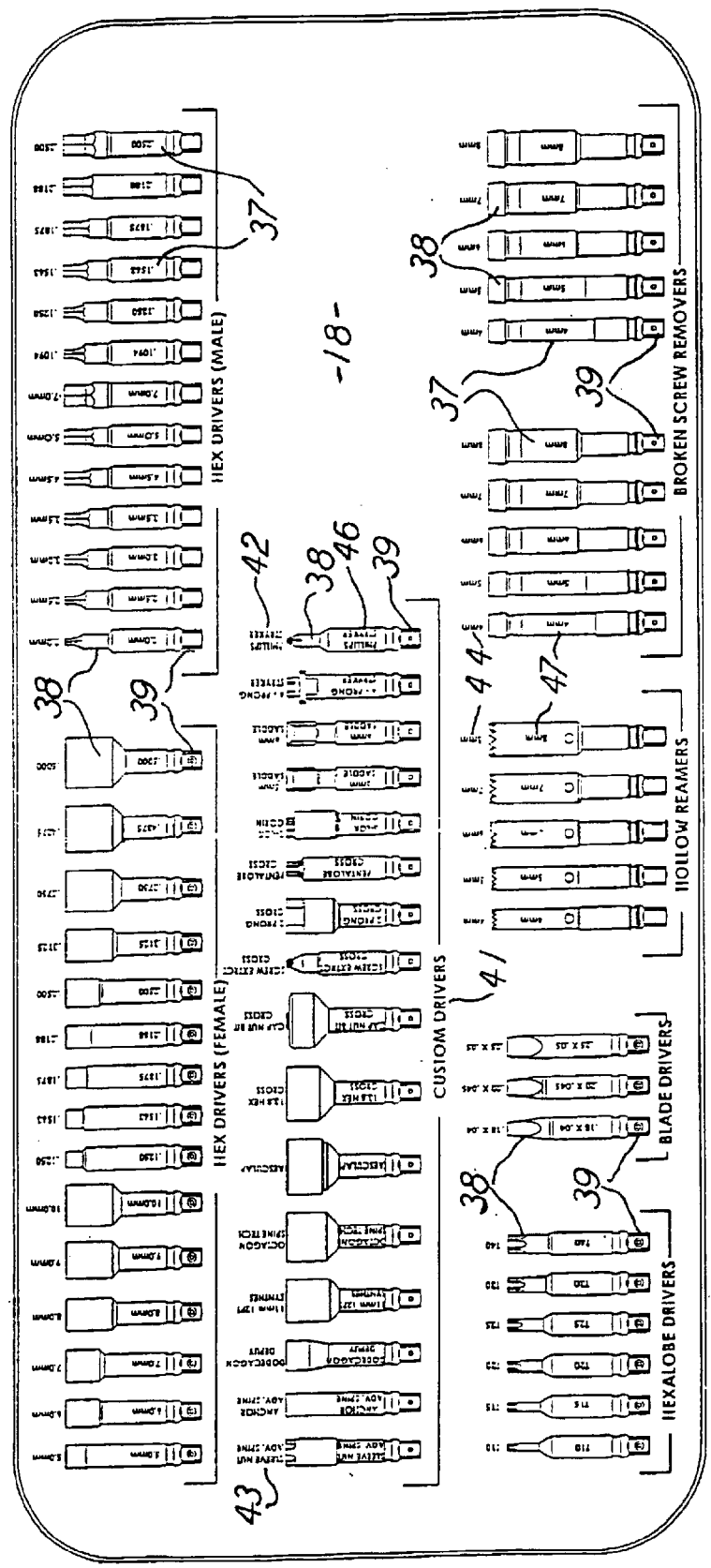
FIG. 7 is a plan view of a portion of the tray of FIG. 6, but showing the indicia on both the tray and the bits thereon.

FIG. 7 also shows that the tray 13 has indicia thereon, such as the "CUSTOM DRIVERS" at 41, for a group of that type of driver. In all, as seen in FIG. 7, there are seven such groups designated by the seven different indicia imprinted, etched or presented on the tray 13, and all are just off the location of the bits themselves so the indicia can always be visible from above. Additionally, the tray 13 has indicia such as "PHILLIPS STRYKER" at 42 thereon, and again the indicia are just off the location of the bits 37 themselves to be visible from above even when the bits 37 are attached in their positions on the tray 13, just as they are shown in FIG. 7. The tray 13 bit size indicia is shown, such as at 44.

Finally, like the floor 18, the bits themselves have the words and numbers for identification of each unique bit. Thus the bits have words thereon such as "PHILLIPS STRYKER" at 46, and they have numbers for sizes, such as numbers at 47, and those words and numbers are permanent on the respective bits 37, and are as seen in FIG. 7.

So the tray 13 has a designated and separated station for each unique bit 37, and the bits 37 themselves have indicia for revealing the type and size or the like. The length of each bit 37 is no greater than required and it thereby avoids extending to conceal the indicia underneath the bit on the floor 18. The entire arrangement is a system of support and presentation for ready access to the bits. To assure the preferred positioning of each bit 37 on the tray 13, the upstanding abutments 33 extend adjacent the ends of the bits 37 which can contact the abutment to establish the longitudinal position of each bit 37 on the tray 13. In actuality, the abutments 33 are considered as a part of the floor 18 and their upper surface 50 can carry the indicia mentioned above. Thus, recognizing that there are three rows of indicia 41 in FIG. 7, and that the abutments 33 occupy the top two rows, the top surfaces 50 of the abutments 33 could carry the indicia 41 and 42 for those two top rows. The abutments 33 are parallel to the respective walls 32, and the abutments are attached to the floor 18. Also, the abutments extends to a height to intersect with regard to the length of the bits 37 for the alignment of the bits, as shown.

Figure 6:
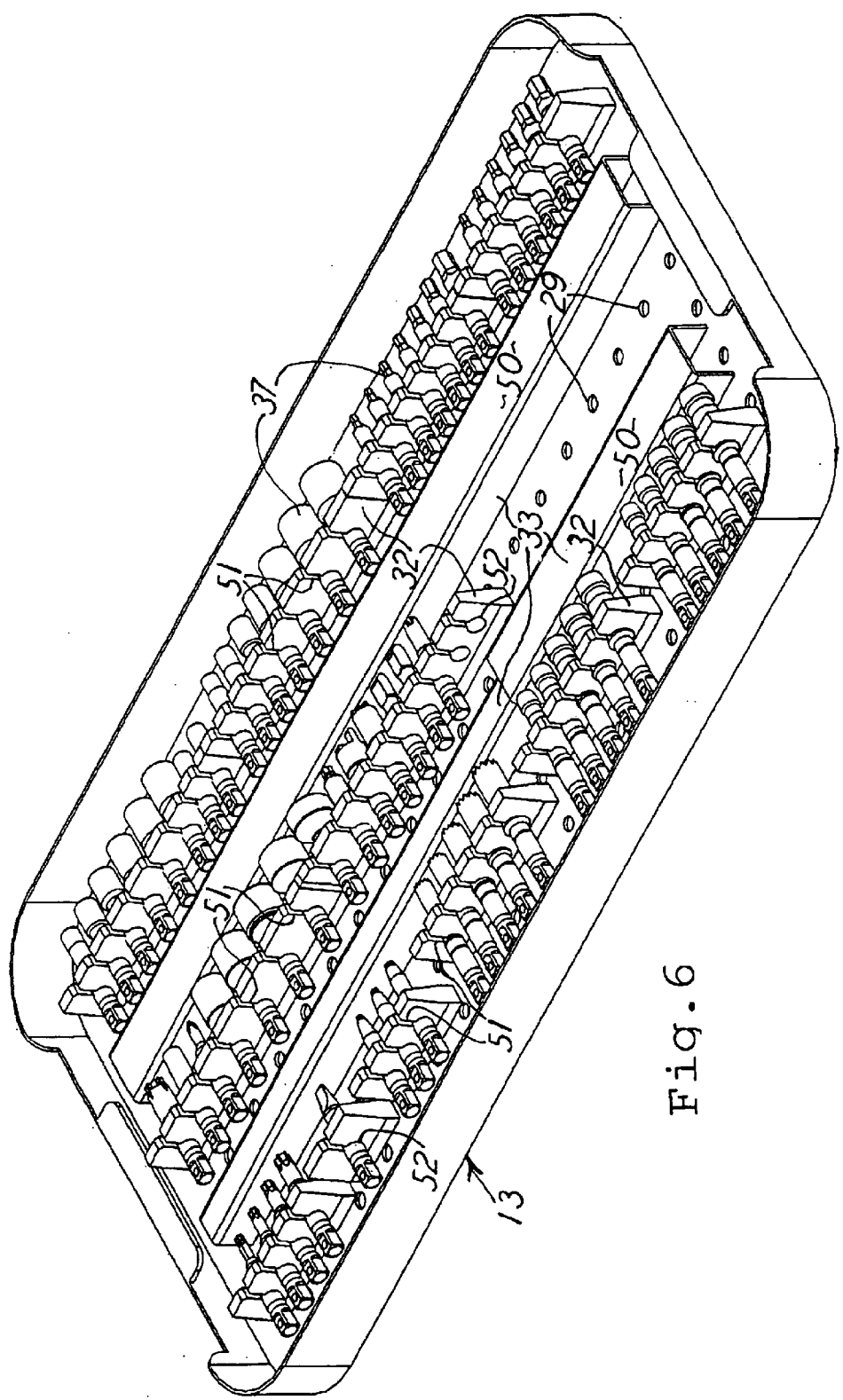
FIG. 6 is an enlarged perspective view of a tray and bits as shown in FIGS. 2 and 3.

The upstanding walls 32 in rows and sections on the tray 13 are of resilient material and suitably attached to the floor 18. Three such walls or rows are shown in FIG. 6. The remainder of the tray 13 is of rigid material. Spaced along in each row 32 are upwardly open slots 51 which communicate with an opening 52 in the wall 32, to form the shape of an inverted key hole. The girth of each bit 37 is slightly greater than the width of the slots 57, and the bit can be pushed down into the slot 51 until it arrives at the hole 52 where the bit is releasably restrained under the friction and resilient hold of the wall 32. The fit between the bit 37 and the hole is snug and of a sufficient length to horizontally support the bits 37 in the positions shown. The resilience of the walls 32, along with the snug fit between the bits 37 and the holes 52, are such that the bits 37 are securely held in the horizontal position shown and can be inserted and removed relative to the walls 32 with ease. Also, any bit 37 in the interior of its row of bits can be accessed by fingering and then tipping for removal from the wall 32, again, that is because of the resiliency. The walls 32 are self supporting in upstanding positions, and the are arranged to flex, tip, and bend in the passage of the bits.

Figure 5:
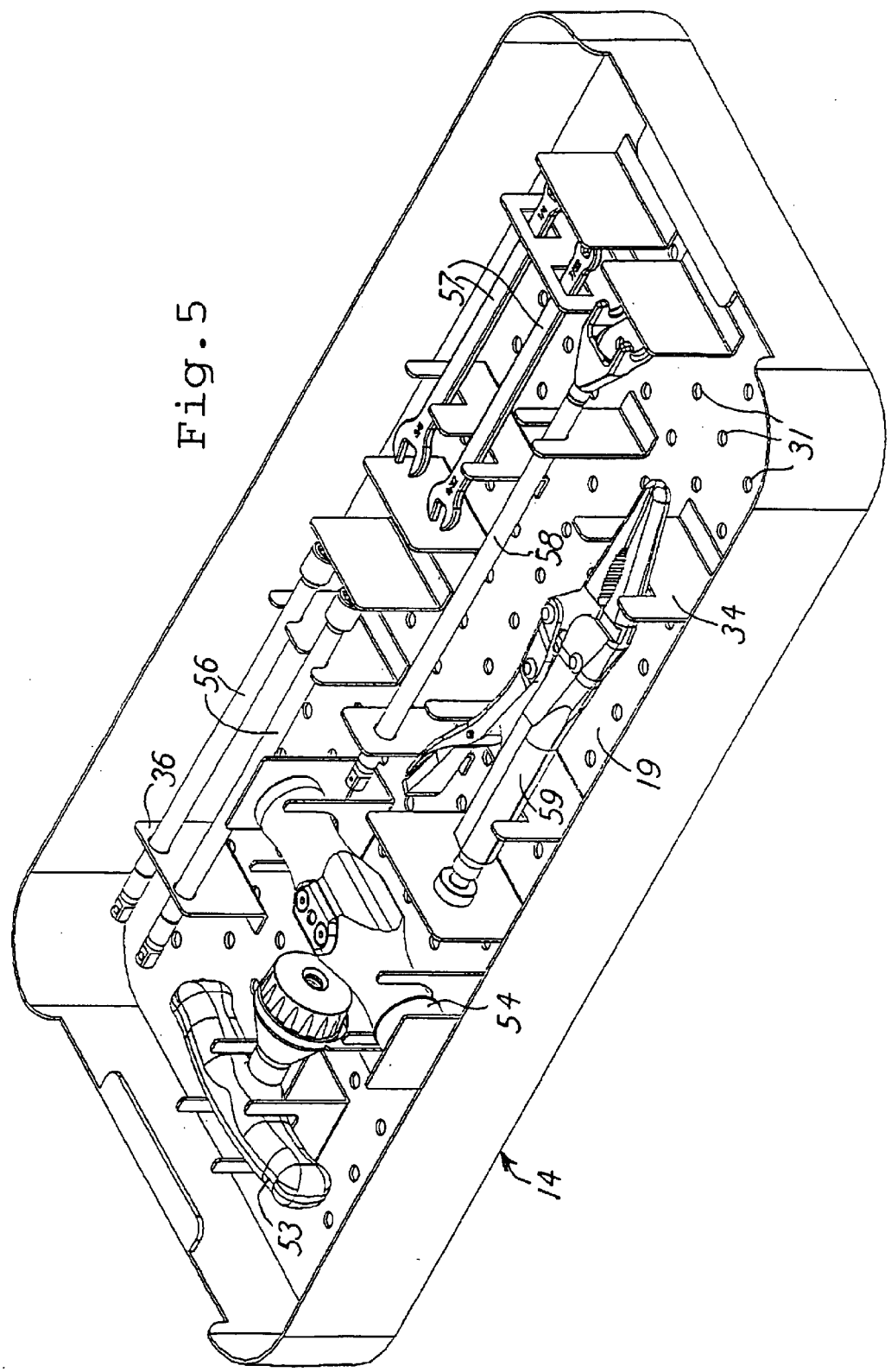
FIG. 5 is an enlarged perspective view of a tray and tools as shown in FIGS. 2 and 3.

Particularly FIG. 5 shows the upper tray 14 with its tools such as the T-handle 53 and the bi-axial handle 54, either one of which could connect to the selected bit 37 for driving the latter. Also, there are extenders 56 useful between the bits 37 and the handles 53 and 54. It will be seen that the extenders 56 are supported by both the supports 34 and are in the holes 36 for more complete support. Other tools on the tray 14 are similarly restrained, such as with the wrenches 57. There is a counter torque drive tool 58, and there is a pliers 59. In that manner, the tools in the tray 14 are restrained from unwanted movement. Also, there is indicia on the tray 14, though unshown herein, adjacent each tool naming the tool as with the bits in the tray 13.

The two trays 13 and 14 can be accessed relative to the base 11, and the necessary assemblage of bit and driving tool can be effected. All items are properly separated until the assembly of two items is made. This permits quick selection and assembly in the midst of surgical procedure. The two trays 13 and 14 are stacked in layers in the box or container 11 to be snug therein by extending throughout the box walls 16. The lower tray has upstanding supports, such as its side walls 21, which upwardly engage and thereby support the upper tray which rests on the surfaces 61 upon which the lower bottom 19 rests. Of course the reverse is true if the tray 14 is the bottom tray, That is, the trays 13 and 14 are universal in girth shape, and either one can be the bottom tray and upwardly support the upper tray.

From the foregoing, it will be understood that there is an inventive method in the arrangement of the labeled rows of bits, and two trays and the positioning of the trays removable from the base or container in the arrangement ready for high-pressure surgical use. Particularly, when a surgeon is acquainted with the kit, the surgeon will know exactly which bit to select for the procedure at hand.

While a specific embodiment and method are disclosed, that is as required by the patent law, and it should be understood and seen that changes can be made without departing from the scope of the invention as defined in the claims.

What is claimed is:

1. A kit of medical tools for removing skeletal screws, comprising:

a box including a base having a bottom and upwardly extending side walls defining an upwardly faced opening, a first tray and a second tray disposed in said box one above the other and extending fully between said side walls, lift portions on both said trays for lifting said trays from said base through said upwardly faced opening, a top removable disposed on said base for enclosing said base and covering said trays in said base, a plurality of screw removing bits, a plurality of bit grippers on said first tray having bit-receiving openings spaced apart on said first tray for releasably restraining said bits against some movement on said first tray, said bits being removably disposed in said bit-receiving openings for separated disposition and ready removal of said bits from said first tray and having portions thereon specially configured for being engaged for rotational driving said bits;

a plurality of tools and with at least some of said tools having portions thereon matching, and thus being mateable with, said special configuration for rotational driving engagement of said bits, and a plurality of tool receptors on said second tray and having tool-receiving openings spaced apart on said second tray and with said plurality of tools separately disposed in said tool receptor openings for restraint against some movement and for separated disposition and ready removal from said second tray.

2. The kit of medical tools, as claimed in claim 1, including:

word and number indicia on said trays respectively and uniquely disposed adjacent said grippers for visibly designating the configuration and sizes of said bits for selectivity by a user of the kit.

3. The kit of medical tools, as claimed in claim 2, wherein:

said bit grippers are resilient for frictionally and releasably gripping said bits.

4. The kit of medical tools, as claimed in claim 3, wherein:

said grippers and said indicia for said bits are respectively grouped in three categories consisting of the words drivers, reamers, and broken screw removers, and each of said indicia groups for said bits in each said category includes revelation of sizes of said bits in the respective said category.

5. The kit of medical tools, as claimed in claim 1, including:

a strip of resilient material on said first tray and upstanding thereon and having a length and spaced apart sections along said length defining said openings between said sections.

6. The kit of medical tools, as claimed in claim 5, including:

said tool receptors having portions upstanding adjacent said tools for contacting and thereby restraining said tools against movement toward and away from said portions.

7. The kit of medical tools, as claimed in claim 1, including:

an abutment attached to said bit tray and extending adjacent said bits for engaging said bits and thereby aligning said bits in a row.

8. The kit of medical tools, as claimed in claim 7, wherein:

said bit grippers extend in a row, and said abutment is upstanding and extends parallel to said row of grippers for abutting said bits to align said bits in gripped condition.

9. A kit of medical tools for removing skeletal screws, comprising:

a box including a base having a bottom and upwardly extending side walls defining an upwardly faced opening, a first tray and a second tray disposed in said box in respective layered upper and lower positions and extending between said side walls, the one of said trays in the lower position having upstanding portions and the one of said trays in the upper position being upwardly supported on said upstanding portions and said trays being removable from said box through said upwardly faced opening, a plurality of screw removing bits, a plurality of bit grippers on said first tray having bit-receiving openings spaced apart on said first tray for restraining said bits against some movement on said first tray, said bits being removably disposed in said bit-receiving openings for separated disposition and ready removal of said bits from said first tray and having portions thereon specially configured for being engaged for rotational driving said bits, a plurality of tools, and a plurality of tool receptors on said second tray and having tool-receiving openings spaced apart on said second tray and with said plurality of tools separately disposed in said tool receptor openings for restraint against some movement and for separated disposition and ready removal from said second tray and with at least some of said tools having portions thereon matching, and thus being mateable with, said special configuration for rotational driving engagement of said bits.

10. The kit of medical tools, as claimed in claim 9, including:

word and number indicia on said trays respectively and uniquely disposed adjacent said grippers for visibly designating the configuration and sizes of said bits for selectivity by a user of the kit.

11. The kit of medical tools, as claimed in claim 10, wherein:

said bit grippers are resilient for frictionally and releasably gripping said bits.

12. A method of arranging a medical kit with bits and tools for removal of screws from bone, comprising the steps of:

producing a plurality of bits for a variety of functional purposes and of differing sizes, labeling said bits according to their functions and sizes, labeling a first tray according to said purposes and said sizes for identifying said bits, positioning bit grippers in a row on said first tray according to and matching with said purposes and said sizes and adjacent said labeling and releasably restraining said bits in said rows, producing a plurality of tools, including at least one of said tools being a universal rotational driver for said bits, releasably supporting said tools on a second tray, and placing both said trays in a container for enclosing said trays for temporary containment of said bits and said tools and having both said trays removable from said container.

13. The method of arranging a medical kit with bits and tools, as claimed in claim 12, including:

placing said trays in said container in stacked relationship with a lower one of said trays having a standard for upwardly supporting an upper one of said trays.

* * * * *